United States Patent [19] [11] 4,112,243
Nowak et al. [45] Sep. 5, 1978

[54] PRODUCTION OF HYDROQUINONE FROM NONAQUEOUS SOLVENT SYSTEMS

[75] Inventors: Edward Norbert Nowak, Uniontown; Lawson Gibson Wideman, Akron; David Alan Hutchings, Stow, all of Ohio

[73] Assignee: The Goodyear Tire & Rubber Company, Akron, Ohio

[21] Appl. No.: 833,203

[22] Filed: Sep. 14, 1977

[51] Int. Cl.$^2$ ............................................. C07C 39/08
[52] U.S. Cl. ..................................... 568/768; 568/811
[58] Field of Search .......... 260/621 C, 621 A, 621 H, 260/625

[56] References Cited
U.S. PATENT DOCUMENTS

| | | |
|---|---|---|
| 3,798,277 | 3/1974 | Sugiyama .......................... 260/621 C |
| 3,884,983 | 5/1975 | Burkholder ....................... 260/621 A |
| 3,895,079 | 7/1975 | Anderson .......................... 260/621 A |
| 3,968,171 | 7/1976 | Burkholder ....................... 260/621 C |
| 4,049,723 | 9/1977 | Tanaka et al. ..................... 260/621 A |

Primary Examiner—James O. Thomas, Jr.
Assistant Examiner—Werren B. Lone
Attorney, Agent, or Firm—D. B. Little

[57] ABSTRACT

A process whereby photograde quality hydroquinone can be separated from the reaction mixture produced by a rearrangement of p-diisopropylbenzene dihydroperoxide, which process comprises the steps of (1) subjecting the mixture to hydrogenation to remove color; (2) concentrating the colorless solution; (3) adding a solvent to the concentrated mixture which dissolves impurities but which causes the hydroquinone to precipitate; and (4) separating the hydroquinone from the supernatant liquid in step (3).

9 Claims, 1 Drawing Figure

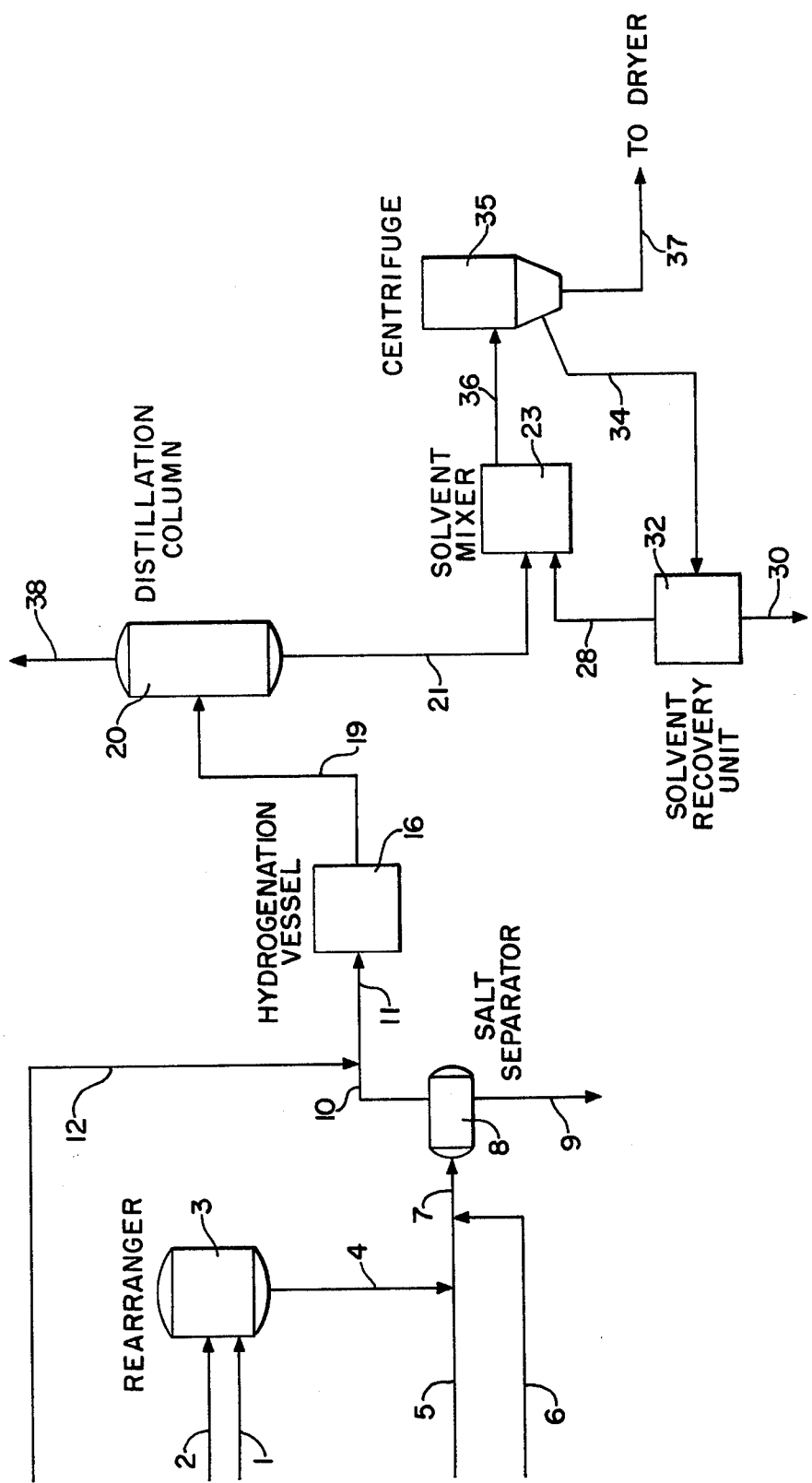

PRODUCTION OF HYDROQUINONE FROM NONAQUEOUS SOLVENT SYSTEMS

BACKGROUND OF THE INVENTION

This invention pertains to the purification of aromatic hydroxy compounds obtained by the cleavage of benzylic hydroperoxides. More particularly, it pertains to a process for purifying hydroquinone made by the cleavage of p-diisopropylbenzene dihydroperoxide.

The state of the present technology is represented by U.S. Pat. Nos. 3,884,983 and 3,968,171. The basic process common to these patents is the acid-catalyzed cleavage or rearrangement of p-diisopropylbenzene dihydroperoxide in a benzene/acetone solvent to hydroquinone and acetone followed by neutralization of the acid catalyst and separation of the hydroquinone from the solvent and by-product impurities.

In U.S. Pat. No. 3,968,171, the separation is accomplished by distilling the acetone off and mixing the distillation bottoms with water; extracting impurities from the bottoms with benzene; and treating the aqueous hydroquinone-containing phase by evaporation, crystallization, centrifugation, and drying.

U.S. Pat. No. 3,884,983 adds the steps of maintaining a reducing atmosphere in the system, carbon treating the concentrated aqueous hydroquinone solution, and purifying recycled water in ion-exchange beds.

Selective hydrogenation of the neutralized rearrangement reactor effluent to prevent formation of polymeric impurities in the distillation step downstream of the reactor is added by U.S. Pat. No. 3,895,079. Hydrogenation of technical grade hydroquinone can produce photograde (high purity) hydroquinone according to German Pat. No. 2,505,271.

Extraction of the aqueous distillation bottoms with a halogenated hydrocarbon (1-3 C) instead of benzene has been proposed as a way to purify hydroquinone in U.S. Pat. No. 3,798,277.

It is thus the purification of the rearranged product which has been the subject of a long continuing effort on the part of those in the field. The reason for this is that the hydroquinone must be a white crystal or crystalline power which meets ASA specification PH 4.126-1962 in order to be photograde. A high standard for whiteness is imperative for photograde material. Hydroquinone is used widely as the main ingredient in black and white film print developing. The purification processes are directed toward improved crystallization and whiteness.

Hydroquinone is also useful as a polymerization inhibitor and as an antioxidant. Hydroquinone itself and derivatives, such as 2,5-di-tert-butylhydroquinone and butylated hydroxyanisole (BHA), are used for the prevention of oxidation in animal or plant fats and aviation fuels.

By-products of the rearrangement reaction, referred to as tars, are believed to be the major impediment to high purity. Among the components of these tars are: p-isopropylphenol, α-hydroxy-p-isopropylphenol, p-diisopropylbenzene, p-isopropenylphenol, isopropenylacetophenone, and dimers and trimers of the product and by-products.

SUMMARY OF THE INVENTION

The process of this invention starts with the known steps of (A) reacting p-diisopropylbenzene dihydroperoxide in a reaction solvent with an acid to form hydroquinone and and acetone; (B) adjusting the pH of the mixture after the reaction to from 2.5 to 5.5 (preferably 3 to 4) by adding a base; (C) precipitating sulfate salts formed in step (B); and (D) separating the precipitated salts from the supernatant mixture. However, the unit operations used for purifying the hydroquinone following step (D) are different than those of the prior art.

Following the salt separation: (a) the reactor effluent is hydrogenated to destroy color-forming impurities and potentially damaging peroxidic chemicals; (b) the hydrogenated stream is distilled to remove essentially all of the acetone and most of the reaction solvent; (c) the concentrated stream, comprising principally hydroquinone, reaction solvent, and tars, is mixed with a solvent in which the tars and residual reaction solvent are soluble but which precipitates the hydroquinone as a pure crystalline product; (d) the resultant two-phase stream is subjected to a solid/liquid separation step such as centrifugation or filtration; (e) the separated solid phase is conveyed to a dryer for conventional handling thereafter; and (f) the liquid phase is subjected to a purification process in order to recycle it back to the mixing step (c).

The hydrogenation step of the instant process is distinguished from that of U.S. Pat. No. 3,895,079 in that it utilizes a nickel catalyst, in particular, Raney nickel, instead of a palladium catalyst supported on alumina, charcoal or silica gel in a fixed bed as does the prior art patent.

The distillation step of this process is also distinguished from the prior art as represented by U.S. Pat. Nos. 3,968,171, 3,884,983 and 3,895,079. In all three of the above-mentioned patents water is added in the distillation step in order to prevent precipitation of solid hydroquinone in the distillation column. Also, the distillation tower bottoms consists of a two-phase stream, one phase being water and hydroquinone, the other containing benzene, hydroquinone, and impurities. Only one of the three aforementioned prior art U.S. Pat. No. (3,895,079) feeds a hydrogenated reactor effluent stream to the distillation column. The distillation herein described, although it does feed a hydrogenated reactor effluent to the distillation column, involves no addition of water to the column. Also, its bottoms stream consists of a one-phase mixture of reaction solvent, hydroquinone and hydrogenated impurities.

Downstream of the distillation column this process comprises the steps of solvent mixing and a solid/liquid separation. The whole system is nonaqueous, alleviating those problems of purity involved with the introduction of water into the system. Hydroquinone, in the presence of water (especially when heated) is subject to degradation to color bodies and polymeric material. The aforementioned prior art patents are all aqueous processes. In addition, the number of steps downstream of the distillation is greater and those types of unit operations which are used (evaporation and crystallization) are much more energy intensive than the unit operations of this process.

DESCRIPTION OF THE DRAWING

The single FIGURE is a diagrammatic representation of the process of the present invention.

DESCRIPTION OF THE PREFERRED EMBODIMENT

As an aid in understanding the process of this invention, the overall process will be described with reference to the flow diagram, with the proviso that this diagram is an exemplary embodiment of the invention and the process is not limited to this particular arrangement. For example, the solid liquid separation step is exemplified by a centrifuge; however, this operation could be done as well by a filter.

Referring then to the drawing, the rearranger feed 1 contains p-diisopropylenzene dihydroperoxide, a reaction solvent (such as a mixture of benzene and acetone), minor amounts of unreacted p-diisopropylbenzene (precursor to the dihydroperoxide) and impurities such as diisopropylbenzene monohydroperoxide and α-hydroxy-α'-hydroperoxy-diisopropylbenzene. The reaction solvent is normally an aromatic hydrocarbon such as benzene, a monoalkylbenzene wherein the alkyl group has from 1-4 carbon atoms, a dialkylbenzene wherein the alkyl group has from 1-4 carbon atoms, a trialkylbenzene wherein the alkyl group has from 1-4 carbon atoms, acetone, or a mixture of acetone with one of the aforementioned hydrocarbons. This feed is mixed in the reactor with the acid catalyst 2 (such as sulfuric acid) in the rearranger 3. A detailed description of the rearrangement reaction can be found in U.S. Pat. No. 3,968,171, col. 3, lines 31-45 which is hereby incorporated by reference into this application.

The rearranger effluent 4 is mixed in-line with ammonia gas which enters via stream 5 and water which enters via stream 6. The ammonia neutralizes the acid catalyst forming ammonium salts which are separated from the combined stream 7 in the salt separator 8. The salt separator consists of a vessel designed so that it has sufficient holding capacity to permit the decantation of the organic phase from the aqueous phase containing the aforementioned salts. Alternatively, this separation may be accomplished by eliminating stream 6 and filtering out the salts. The aqueous phase along with the precipitated salts is removed from the salt separator either on a continuous or batchwise basis via stream 9.

The organic stream 10 exists the salt separator and is mixed with hydrogen under pressure 12, and the combined stream 11 enters the hydrogenation vessel 16. This vessel contains the hydrogenation catalyst and operates at a pressure ranging from atmospheric pressure to 1,400 kilopascals (KPa).

The effluent from the hydrogenation vessel 19 flows on to distillation column 20. The distillation is carried out so as to concentrate the hydrogenated stream in preparation for the solvent mixing step. Essentially all of the acetone and most of the reaction solvent are distilled ovehead as stream 38. The concentrated bottoms stream 21 flows on to the solvent mixer 23.

The solvent mixer 23 is the first step in a process loop represented by the mixer, the centrifuge 35 and the solvent recovery unit 32. Circulating within this loop is the solvent which is unique in that it will dissolve the hydrogenated impurities and will mix with the reaction solvent, but it will precipitate the hydroquinone owing to a very low solubility of hydroquinone in the solvent. The solvent enters the solvent mixer via stream 28 and the two-phase stream 36 (containing solid hydroquinone and the solvent containing reaction solvent and tars) flows on to the solid/liquid separation step shown as a centrifuge 35 on the drawing.

Following centrifuge 35, the hydroquinone wet cake 37 is conveyed to a dryer. The centrifuge filtrate 34 containing solvent, reaction solvent, and tars flows to the solvent recovery unit 32.

The function of the solvent recovery unit is to purify the spent solvent so that it may be recycled to the solvent mixer. This purification may be done by any suitable unit operation such as distillation or evaporation. The tars exit the loop via stream 30.

Suitable reaction conditions for the hydrogenation are: 20° to 100° C., atmospheric pressure to 1400 KPa, and reaction time of from 2 minutes to 1 hour. The conditions of temperature, pressure and reaction time found best suited to hydrogenation in this process are approximately 20 to 30° C. atmospheric pressure, and 15 minutes respectively. A suitable hydrogenation catalyst is nickel, more particularly Raney nickel.

The solvent used to selectively dissolve the rearrangement product impurities but little or none of the hydroquinone can be chosen from the following list of solvents: methylene chloride; carbon tetrachloride; 1,1,2-trichloroethane; trichloroethylene; fluoro-chlorocarbons containing 1-4 carbon atoms; fluorocarbons containing 2-6 carcarbon atoms; n-pentane; n-hexane; n-heptane; isomers of n-pentane, n-hexane and n-heptane; and cyclohexane.

The amount of solvent required to precipitate hydroquinone is dependent on solvent used and the degree of concentration of the neutralized rearrangement product. The ratio of concentrated neutralized rearrangement product, stream 21, to solvent can vary from 1/1 to 1/50 (volume ratio).

The following examples are given to illustrate and not to limit the invention. Unless otherwise stated, percent means weight percent.

Before beginning the examples it should be explained that one of the measurements of hydroquinone purity is color number. Color number is an arbitrary color measurement obtained by comparing a five percent hydroquinone solution in a dilute acetic acid with a known set of color standards. The color standard is a platinum/cobalt standard of the American Public Health Association (APHA). A standard color number curve is plotted using various solutions of the standard. As furnished, the standard has a color number of 500. A 1 percent solution would then have a color number of five, etc. Measurements of light absorbance are made on an instrument such as a Beckman Spectrophotometer at a wave length of 390. For hydroquinone, a color number of less than or equal to 20 corresponds to commercially available photograde hydroquinone and does meet the ASA specification PH 4.126-1962 for color and acetone solubility.

EXAMPLE I

Rearrangement Technique

One hundred cubic centimeters of acetone and 1.5 grams of $H_2SO_4$ were added to a three-neck flask fitted with a reflux condenser, thermometer and dropping funnel. The system was then heated to reflux. The dropping funnel was then charged with 200 cubic centimeters (170 grams) of rearranger feed comprised of roughly 24 percent p-diisopropylbenzene dihydroperoxide, 35 percent acetone and 31 percent benzene, the remainder consisting essentially of minor amounts of p-diisopropylbenzene monohydroperoxide, α-hydroxy-α'-hydroperoxy diisopropylbenzene and p-diisopropylbenzene, and one cubic centimeter of 50 weight percent hydrogen peroxide to convert α-hydroxy-α'-hydroperoxy diisopropylbenzene to p-diisopropylbenzene dihydroperoxide and thus improve the yield. The contents of the dropping funnel were then slowly added to the reaction mixture in the flask. After complete addition of the feed, the reaction was allowed to proceed for an additional 20 minutes. At this time, the pH of the solution was raised to approximately 3 to 3.5 with concentrated NH$_4$OH. The resulting ammonium sulfate precipitate was then filtered from the rearranged product.

The deep orange-yellow color of the neutralized rearranger product was effectively removed by nickel catalysts under very mild hydrogenation conditions. The nickel catalyst was found to give improved results under lower hydrogen pressure and shorter reaction time. Hydrogen pressure in excess of 200 psig (1,378 KPa) tends to over-reduce the feed and the formation of 1,4-cyclohexanediol becomes appreciable. The reaction time is highly dependent upon the hydrogen pressure and reaction temperature employed. If one atmosphere of hydrogen pressure is used at 25° C., a reaction time of 15 minutes is normally sufficient to clarify the feed. The following examples are illustrative.

EXAMPLE II

A one-liter stainless steel reactor was flushed with nitrogen and charged with 5.0 gram of modified T-1 Raney nickel suspended in 250 milliliters of the neutralized rearranger feed. Modified Raney nickel and its preparation are described in U.S. Pat. No. 3,953,511, column 3, line 33 through column 4, line 13 which is hereby incorporated by reference into this application. The reactor was then charged with hydrogen to a pressure of 1,378 kilopascals (200 psig) and the temperature was maintained at 25° C. with internal cooling coils, as stirring was continued for 1 hour. The reaction mixture was gravity filtered in the atmosphere to give a water-white solution that upon work-up gave hydroquinone with a color number of 27.0.

EXAMPLE III

The catalyst from Example I was recycled with a new batch of neutralized rearranger feed and a reaction was carried out similar to Example II except that the hydrogen pressure was maintained at 689 kilopascals (100 psig) and the reaction was carried out for 15 minutes. The hydroquinone thus obtained gave a color number of 18.5.

EXAMPLE IV

A 200-milliliter solution of neutralized rearranger effluent was charged into a one-liter stainless steel reactor with five grams of modified T-1 nickel catalyst. The reactor was charged with 50 psig (345 KPa) of hydrogen and heated to 60° C. for 30 minutes with stirring. After the standard work-up, e.g. precipitation with CH$_2$Cl$_2$, hydroquinone with a color number of 7 was produced.

EXAMPLE V

A stainless steel reactor (1-liter volume) was charged with a granular form (6.4 millimeter × 3.2 millimeter nominal size, suitable for fixed-bed catalysis) of modified T-1 nickel catalyst and 200 milliliters of neutralized rearranger effluent. The reactor was swept with hydrogen and a blanket of hydrogen was maintained over the reactor contents for 10 minutes at 25° C. The hydrogen atmosphere was maintained by passing a slow stream of hydrogen over the contents at zero reactor gauge pressure (atmospheric pressure). Hydroquinone, after work-up, was produced with a color number of 4.

EXAMPLE VI

A 500 milliliter Erlenmeyer flask, which was equipped with a magnetic stirrer and hydrogen balloon, was charged with 250 milliliters of neutralized rearranger effluent and 5 grams of modified T-1 nickel catalyst. The contents of the flask were stirred for two minutes at 25° C. with one atmosphere of hydrogen. After work-up, hydroquinone with a color number of 13 was produced.

EXAMPLE VII

Solvent Technique for Hydroquinone Recovery

One liter stainless steel reactor was flushed with nitrogen and charged with 5.0 grams of modified T-1 Raney nickel suspended in 300 milliliter of neutralized rearranger product. The reactor was then charged with hydrogen to a pressure of 552–690 KPa, and the temperature was maintained at 25° C. with internal cooling coils as stirring was continued for 15 minutes. The reaction mixture was gravity filtered in the atmosphere to give a water-white solution. The hydrogenated rearrangement product was placed into a rotary evaporator and concentrated from a volume of 300 cubic centimeters to a volume of 25 to 30 cubic centimeters. At this point 50 cubic centimeters of methylene chloride was added to the sample with stirring. A white crystalline product (hydroquinone) was precipitated. The precipitate was filtered to give 7.5 grams of hydroquinone having a color number of 17.5 and a 99.71 percent purity.

While certain representative embodiments and details have been shown for the purpose of illustrating the invention, it will be apparent to those skilled in this art that various changes and modifications may be made therein without departing from the spirit or scope of the invention.

What is claimed is:

1. In a process for making hydroquinone comprising the steps of
   (a) reacting a feed stream comprising p-diisopropylbenzene dihydroperoxide
      (1) in a reaction solvent selected from the group consisting of benzene, monoalkyl benzenes wherein the alkyl group has from 1-4 carbon atoms (1-4C), dialkyl benzenes wherein the alkyl groups have 1-4C, trialkyl benzenes wherein the alkyl groups have 1-4C, mixtures of the aforesaid aromatics with acetone and acetone
      (2) with an acid selected from the group consisting of H$_3$PO$_4$, HClO$_4$, p-toluene-sulfonic acid, SO$_2$, HBF$_4$, H$_2$SiF$_6$, BF$_3$ and any other Lewis acid
      (3) in the temperature range of about 50° to 100° C. to form hydroquinone and acetone;
   (b) adjusting the pH of the mixture after the reaction to from 2.5 to 5.5 by adding a base, thereby causing acid salts to form and precipitate;
   (c) separating the precipitated salts from the supernatant mixture; wherein the improvement comprises the steps of:
   (d) hydrogenating the supernatant from step (c) with a Raney nickel catalyst to remove color;

(e) concentrating the mixture of step (d);

(f) adding to the concentrated mixture a solvent selected from the group consisting of methylene chloride, carbon tetrachloride, 1,1,2-trichloroethane, trichloroethylene, fluorocarbons containing 2-6 carbon atoms, fluoro-chlorocarbons containing 1-4 carbon atoms, pentane, hexane, heptane, and cyclohexane, thereby causing hydroquinone crystals to precipitate; and (g) separating the hydroquinone from the supernatant liquid in step (f).

2. The process as recited in claim 1 wherein the feed stream contains minor amounts of $\alpha$-hydroxy, $\alpha'$-hydroperoxy-diisopropylbenzene and hydrogen peroxide is added in step (a) to convert it to p-diisopropylbenzene dihydroperoxide which in turn is converted to hydroquinone, thus increasing the reaction yield.

3. The process as recited in claim 1 further comprising the step of distilling the supernatant liquid from step (g) in order to purify the solvent and recycling said solvent back to step (f).

4. The process as recited in claim 1 wherein the reaction solvent in step (a) is comprised of a mixture of benzene and acetone, and the pH is adjusted to a value from 3 to 4 in step (b).

5. The process as recited in claim 4 wherein step (c) is accomplished by filtration.

6. The process as recited in claim 4 wherein the pH adjustment in step (b) is accomplished by adding ammonia and water to the reactor effluent stream and the separation in step (c) is accomplished by decanting the salt-containing aqueous phase from the organic phase which both flow together from step (b).

7. The process as recited in claim 6 wherein the separation in step (g) is accomplished by centrifugation.

8. The process as recited in claim 7 wherein the hydrogenation is accomplished by a catalytic reaction wherein the hydrogenation (d) conditions are: 20°–100° C., atmospheric pressure to 1400 kPa, and reaction time of 2 minutes to 1 hour; and wherein the solvent in step (f) is methylene chloride.

9. The process as recited in claim 8 wherein the hydrogenation catalyst is modified T-1 Raney nickel and wherein the hydrogenation step is carried out at atmospheric pressure at a temperature of from 20° to 30° C.

* * * * *